(12) United States Patent
Ono et al.

(10) Patent No.: US 9,125,561 B2
(45) Date of Patent: Sep. 8, 2015

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Shigeaki Ono, Tokyo (JP); Yukio Sakagawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 2 days.

(21) Appl. No.: 13/974,100

(22) Filed: Aug. 23, 2013

(65) Prior Publication Data

US 2014/0063451 A1    Mar. 6, 2014

(30) Foreign Application Priority Data

Aug. 30, 2012 (JP) ................................. 2012-190592

(51) Int. Cl.
*A61B 3/12* (2006.01)
*A61B 3/00* (2006.01)
*A61B 3/10* (2006.01)

(52) U.S. Cl.
CPC ................ *A61B 3/0058* (2013.01); *A61B 3/102* (2013.01)

(58) Field of Classification Search
CPC .......... A61B 3/102; A61B 3/12; A61B 3/152; A61B 5/0073
USPC ............................. 351/206, 246, 205; 382/131
See application file for complete search history.

(56) References Cited

U.S. PATENT DOCUMENTS

| 7,789,511 | B2 * | 9/2010 | Aoki et al. ..................... 351/205 |
| 2008/0151187 | A1 | 6/2008 | Tsukada et al. |
| 2010/0194757 | A1 | 8/2010 | Tomidokoro et al. |

FOREIGN PATENT DOCUMENTS

| CN | 101049230 A | 10/2007 |
| CN | 101084824 A | 12/2007 |
| CN | 101095610 A | 1/2008 |
| CN | 101204318 A | 6/2008 |
| CN | 101251365 A | 8/2008 |
| CN | 101254090 A | 9/2008 |
| JP | 2008-209166 A | 9/2008 |

OTHER PUBLICATIONS

Great Britain Search Report issued in corresponding application No. GB1315281.4 on Feb. 25, 2014.
Chinese Office Action issued in corresponding application No. 201310389177.0 on Feb. 15, 2015.

* cited by examiner

*Primary Examiner* — Hung Dang
(74) *Attorney, Agent, or Firm* — Carter, DeLuca, Farrell & Schmidt, LLP

(57) ABSTRACT

For appropriately obtaining the tomographic image and the layer thickness map are provided in a short period of time regardless of involuntary eye movement, when the tomographic image is to be obtained in a specific scan pattern, a 3D tomographic image is first obtained by 3D scan, and then a tomographic image of a desired part is extracted from the image in accordance with the specific scan pattern. Further, based on the obtained 3D tomographic image, a sector for layer thickness map display, a main scanning line, and a sub-scanning line, which are displayed on a fundus image, are set movable, and tomographic images taken along both the scanning lines after the movement are obtained. The sector having a center corresponding to the intersection between those scanning lines and the layer thickness map are recalculated and displayed so as to follow the intersection.

40 Claims, 9 Drawing Sheets

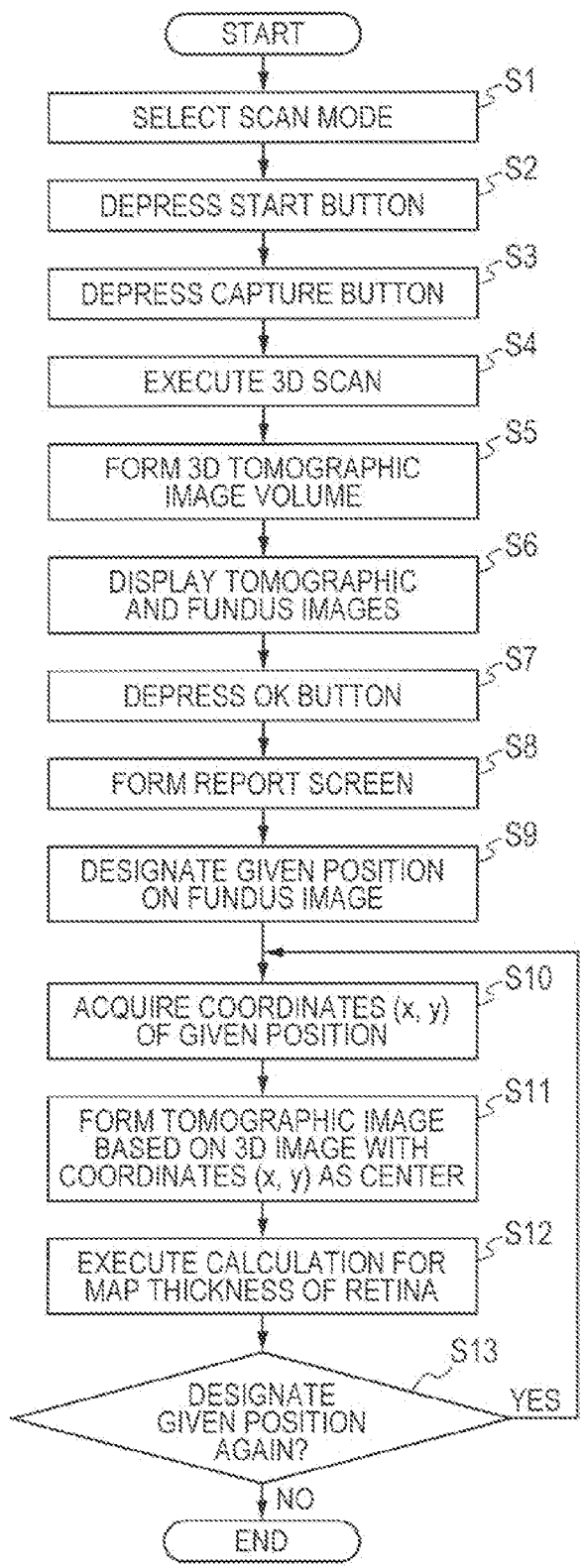

IMAGE PROCESSING APPARATUS, IMAGE PROCESSING METHOD, AND PROGRAM

BACKGROUND OF THE INVENTION

1. Field of the Invention

The present invention relates to a method and apparatus for processing an image obtained in an ophthalmologic apparatus configured to observe, image, and to measure an eye to be inspected, and to a program therefor.

2. Description of the Related Art

Currently, there are various types of opthalmological instruments using an optical instrument. For instance, as an optical instrument for observing an eye, there are used various instruments such as an anterior eye part imaging instrument, a fundus camera, a confocal laser scanning opthalmoscope (scanning laser opthalmoscope: SLO), and the like. In particular, an optical tomographic imaging apparatus, which performs optical coherence tomography (OCT) utilizing an interference phenomenon of multi-wavelength light, is an apparatus capable of obtaining a tomographic image of a sample with high resolution. For this reason, the optical tomographic imaging apparatus is becoming an indispensable apparatus as an opthalmological instrument for a specialist of retina in the outpatient field. The optical tomographic imaging apparatus is hereinafter referred to as an OCT apparatus.

The OCT apparatus is capable of splitting measuring light having low coherence into reference light and measuring light, and irradiating an object to be inspected with the measuring light to cause return light from the object to be inspected to interfere with the reference light, to thereby measure a layer of the object to be inspected. Further, the OCT apparatus can obtain a tomographic image with high resolution by scanning the measuring light on the sample. Therefore, the tomographic image of a retina of the fundus of the eye to be inspected is acquired to be widely used for ophthalmologic diagnosis of the retina and the like.

Japanese Patent Application Laid-Open No. 2008-209166 proposes a general ophthalmologic apparatus in which the OCT scans the fundus by moving a galvanometer mirror based on a scan pattern designated by an operator.

During diagnosis of the eye to be inspected, for example, there are cases where the thickness of each layer at an intended part or in the vicinity thereof based on the tomographic image of the retina layer or the like is required as accompanying information. There has been known a method of arranging a sector for determining a plurality of regions in the fundus image, and displaying an average layer thickness in each region in the sector, to thereby meet the demand.

However, a method of adaptively displaying, along with the movement of the sector, the tomographic image at a position at which the sector is located is unknown, and it has been difficult to compare, when the sector is moved to a given position, the layer thickness in the region in which the sector is arranged and the tomographic image at the position at which the sector is arranged.

SUMMARY OF THE INVENTION

The present invention has been made in view of the above-mentioned situations, and has an object to enable comparison with ease between, when a sector is moved to a given position, a layer thickness in a region in which the sector is arranged and a tomographic image at a position at which the sector is arranged.

In order to solve the above-mentioned problem, according to one aspect of the present invention, there is provided an image processing apparatus, including: a fundus image acquiring unit for acquiring a fundus image of an eye to be inspected; a calculating unit for calculating a thickness of a predetermined layer of a fundus of the eye to be inspected in a partial region on the fundus image; a tomographic image acquiring unit for acquiring a tomographic image of the fundus in the partial region; a display control unit for causing a display unit to display the fundus image, a display form representing the partial region, and the tomographic image; and a changing unit for changing a position of the display form representing the partial region, the display form being displayed on the display unit, the tomographic image acquiring unit being configured to acquire, when the position of the display form representing the partial region is changed, a tomographic image of the fundus of the eye to be inspected in the partial region after the position is changed, the display control unit being configured to cause the display unit to display the tomographic image in the partial region after the position is changed instead of the tomographic image in the partial region before the position is changed.

According to one aspect of the present invention, there is also provided an image processing apparatus, including: an acquiring unit for acquiring a tomographic image group including a plurality of tomographic images that are acquired at different positions of an object to be inspected; a forming unit for forming, based on the tomographic image group, as a formed image, an image arranged so as to intersect with at least one of the plurality of tomographic images; a sector forming unit for forming, based on the tomographic image group, a sector for sectioning the formed image, and displaying, as a map, a thickness of a predetermined layer of the object to be inspected in a region sectioned by the sector; a display control unit for causing a display unit to display the formed image and the sector; a center position designating unit for designating a formed image center position serving as a center position of the formed image; and an aligning unit for aligning the formed image center position and a center position of the sector for sectioning the formed image, the sector forming unit being configured to recalculate the thickness of the predetermined layer to be displayed as a map in accordance with the alignment of the center position of the sector, and to cause the display unit to display the map.

In order to solve the above-mentioned problem, according to one aspect of the present invention, there is further provided an image processing method, including: acquiring a tomographic image group including a plurality of tomographic images that are acquired at different positions of an object to be inspected and extend in parallel to each other; forming, as a formed image, an image arranged so as to intersect with at least one of the plurality of tomographic images, based on the tomographic image group; forming a sector for sectioning the formed image, and for displaying, as a map, a thickness of a predetermined layer of the object to be inspected in a region sectioned by the sector, based on the tomographic image group; causing a display unit to display the formed image and the sector; and aligning a formed image center position serving as a designated center position of the formed image and a center position of the sector for sectioning the formed image, the forming a sector including recalculating the thickness of the predetermined layer to be displayed as a map in accordance with the alignment of the center position of the sector, and causing the display unit to display the map.

According to the embodiments of the present invention, it becomes possible to present the partial tomographic image in a short amount of time and suitably display the layer thickness distribution along therewith.

Further features of the present invention will become apparent from the following description of exemplary embodiments with reference to the attached drawings.

BRIEF DESCRIPTION OF THE DRAWINGS

FIG. 9 is a flow chart illustrating an imaging and report forming operation in the first embodiment.

DESCRIPTION OF THE EMBODIMENTS

First Embodiment

The present invention is described in detail based on embodiments illustrated in FIGS. 1A to 10.

Schematic Configuration of Apparatus

A schematic configuration of a fundus inspecting apparatus according to this embodiment is described with reference to FIG. 1A.

Figure 1A:
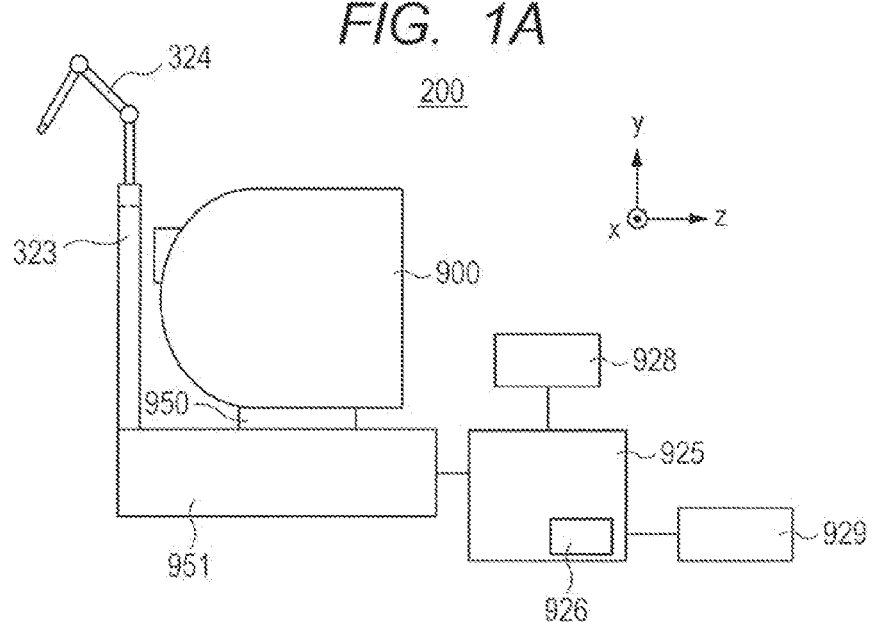
FIGS. 1A and 1B are structural views of an OCT apparatus according to a first embodiment of the present invention.

FIG. 1A is a side view of an ophthalmologic apparatus. An ophthalmologic apparatus (fundus inspecting apparatus) 200 includes an optical head 900 that is a measuring optical system for taking an anterior ocular segment image and a two-dimensional image and a tomographic image of a fundus, and a stage portion 950 that is a movable portion capable of moving the optical head through use of motors (not shown) in xyz directions in FIG. 1A. A base portion 951 contains a spectrometer (described later).

A personal computer 925, which also serves as a control portion of a stage portion, controls the stage portion and configures a tomographic image. A storage unit 926 also serves as a subject information storage portion and stores a program for taking a tomographic image. A monitor 928 serves as a display portion, and an input portion 929 gives an instruction to the personal computer. Specifically, the input portion 929 includes a keyboard and a mouse. A jaw holder 323 holds a jaw and a forehead of a subject to urge the subject to fix an eye (eye to be inspected). An external fixation lamp 324 is used for fixing the eye of the subject.

Figure 1B:
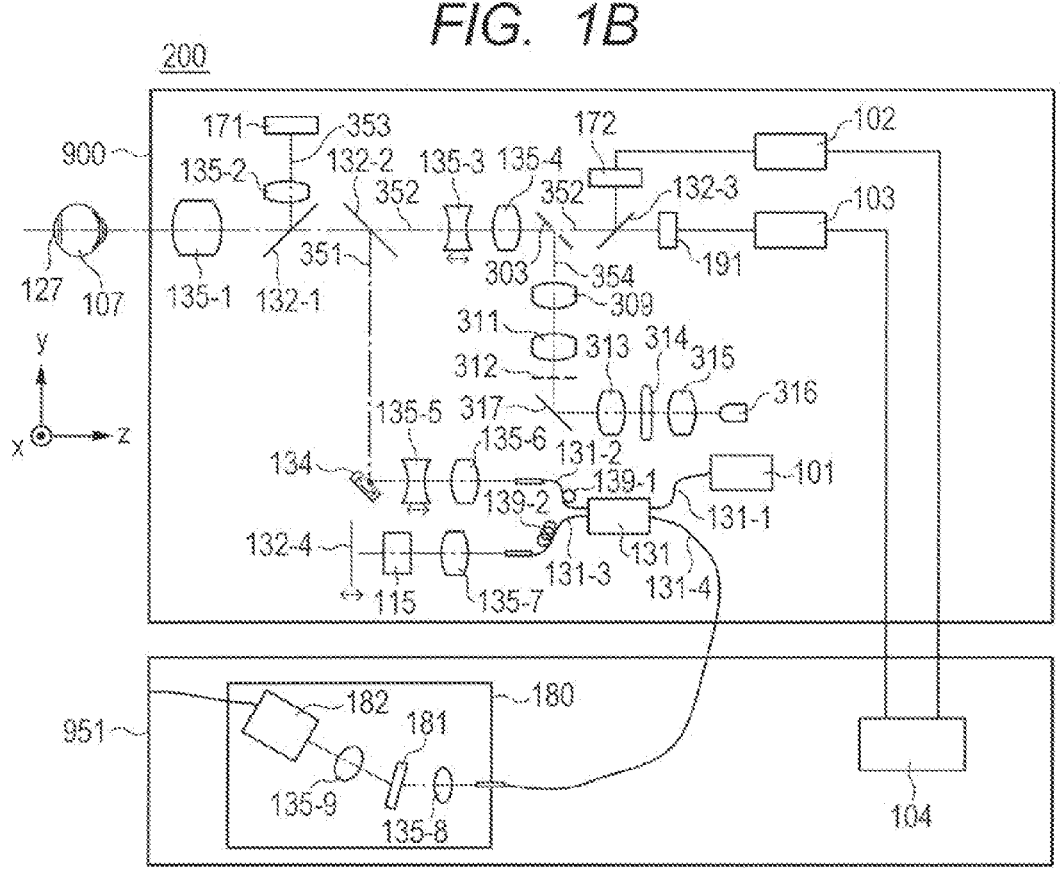

Configurations of the measuring optical system and the spectrometer of this embodiment are described with reference to FIG. 1B.

First, an inside of the optical head 900 part is described. An objective lens 135-1 is set so as to be opposed to an eye 107 to be inspected, and an optical path on an optical axis thereof is branched into an optical path 351 of an OCT optical system, an optical path 352 for fundus observation and fixation lamp, and an optical path 353 for anterior ocular segment observation depending on the wavelength band by a first dichroic mirror 132-1 and a second dichroic mirror 132-2. Out of lenses 135-3 and 135-4, the lens 135-3 is driven by a motor (not shown) for focus adjustment for a fixation lamp 191 and a CCD 172 for fundus observation.

Between the lens 135-4 and a third dichroic mirror 132-3, a perforated mirror 303 is arranged, and the optical path 352 is branched into the optical path 352 and an optical path 354.

The optical path 354 forms an illuminating optical system for illuminating the fundus of the eye 107 to be inspected. On the optical path 354, there are arranged an LED light source 316 serving as an illuminating light source for fundus observation that is used for positioning the eye 107 to be inspected, and a strobe tube 314 that is used for imaging the fundus of the eye 107 to be inspected. Condenser lenses 313 and 315 and a mirror 317 are further arranged on the optical path 354. Illuminating light emitted from the LED light source 316 and the strobe tube 314 is shaped into a ring-like light flux by a ring slit 312 and is reflected by the perforated mirror 303 so as to illuminate a retina 127 of the eye 107 to be inspected. Lenses 309 and 311 are further arranged on the optical path 354. The LED light source 316 has a central wavelength approximately around 780 nm, for example.

Behind the perforated mirror 303 on the optical path 352, the optical path 352 is branched by the third dichroic mirror 132-3 into an optical path to the CCD 172 for fundus observation and an optical path to the fixation lamp 191 depending on the wavelength band as described above.

The CCD 172 has sensitivity corresponding to a central wavelength of the LED light source 316 that emits illumination light for fundus observation, specifically, approximately around 780 nm in this embodiment. The CCD 172 is connected to a CCD control portion 102. On the other hand, the fixation lamp 191 generates visible light to urge the subject to fix the eye. The fixation lamp 191 is connected to a fixation lamp control portion 103.

The CCD control portion 102 and the fixation lamp control portion 103 are connected to a computing portion 104, and data is input and output via the computing portion 104 to and from the personal computer 925.

A lens 135-2 and an infrared CCD 171 for anterior ocular segment observation are provided on the optical path 353. The CCD 171 has sensitivity corresponding to a wavelength of illumination light for anterior ocular segment observation (not shown), for example, approximately around 970 nm. Further, an image splitting prism (not shown) is arranged on the optical path 353. Thus, a distance in the z direction of the optical head 900 part with respect to the eye 107 to be inspected can be detected as a split image in the anterior ocular segment observation image.

The optical path 351 forms the OCT optical system as described above and is used for taking a tomographic image of the fundus of the eye 107 to be inspected. An XY scanner 134 scans light on the fundus. The XY scanner 134 is illustrated as a single mirror, but performs scanning in 2-axis directions of X and Y. Out of lenses 135-5 and 135-6, the lens 135-5 is driven by a motor (not shown) for adjusting focus of light emitted from a light source 101 through a fiber 131-2 connected to an optical coupler 131 onto the fundus of the eye 107 to be inspected. Owing to the focus adjustment, the light from the fundus of the eye 107 to be inspected simultaneously forms an image in a spot shape to enter an end of the fiber 131-2.

Next, configurations of an optical path from the light source 101, a reference optical system, and the spectrometer are described.

The configurations include the optical source 101, a mirror 132-4, a dispersion compensation glass 115, the optical coupler 131 described above, optical fibers 131-1 to 131-4 in a single mode connected to the optical coupler 131 to be integrated, a lens 135-7, and a spectrometer 180.

The above-mentioned components constitute a Michelson interferometer. The light emitted from the light source 101 is split into measuring light on the optical fiber 131-2 side and reference light on an optical fiber 131-3 side through the optical fiber 131-1 via the optical coupler 131.

The measuring light illuminates the fundus of the eye 107 to be inspected to be observed through the optical path of the OCT optical system described above and reaches the optical coupler 131 through the same optical path due to reflection and scattering by a retina.

On the other hand, the reference light reaches the mirror 132-4 through the optical fiber 131-3, the lens 135-7, and the dispersion compensation glass 115 inserted for matching the dispersion of the measuring light with that of the reference light, and is reflected from the mirror 132-4. Then, the reference light returns through the same optical path and reaches the optical coupler 131.

The optical coupler 131 combines the measuring light with the reference light to form interference light. In this case, interference occurs when an optical path length of the measuring light and an optical path length of the reference light become substantially equal to each other. The mirror 132-4 is held so as to be adjusted in an optical axis direction by a motor and a drive mechanism (not shown) and is capable of adjusting the optical path length of the reference light to that of the measuring light varying depending on the eye 107 to be inspected. The interference light is guided to the spectrometer 180 through the optical fiber 131-4.

Further, a polarization adjusting portion 139-1 is provided for the measuring light in the optical fiber 131-2. A polarization adjusting portion 139-2 is provided for the reference light in the optical fiber 131-3. Those polarization adjusting portions each have a part in which the optical fiber is looped several times. This looped part is rotated about the longitudinal direction of the fiber to twist the fiber. In this manner, the polarization state of each of the measuring light and the reference light can be adjusted and matched to each other. In this apparatus, the polarization state of each of the measuring light and the reference light is adjusted in advance and fixed.

The spectrometer 180 includes lenses 135-8 and 135-9, a diffraction grating 181, and a line sensor 182.

The interference light emitted from the optical fiber 131-4 is substantially collimated through the lens 135-8 and dispersed by the diffraction grating 181 to form an image on the line sensor 182 by the lens 135-9.

Next, the periphery of the light source 101 is described. The light source 101 is a super luminescent diode (SLD) that is a typical low coherent light source. Light emitted from the light source 101 has a central wavelength of 855 nm and a wavelength band width of about 100 nm. In this case, the band width influences a resolution in an optical axis direction of a tomographic image to be acquired, and hence, is an important parameter. Further, although the SLD is selected, the type of the light source 101 is not particularly limited as long as the light source is capable of emitting low coherent light, and amplified spontaneous emission (ASE) or the like may also be used. Considering the measurement of an eye, near-infrared light is suitable for the central wavelength. Further, it is desired that the central wavelength be a shortest possible wavelength because the central wavelength influences a resolution in a lateral direction of a tomographic image to be acquired. For both the reasons, the central wavelength is set to 855 nm, as an example.

Although the Michelson interferometer is used as an interferometer in this embodiment, a Mach-Zehnder interferometer may be used. It is desired that the Mach-Zehnder interferometer be used in the case where an optical amount difference between the measuring light and the reference light is large, and the Michelson interferometer be used in the case where the optical amount difference is relatively small.

Figure 10:
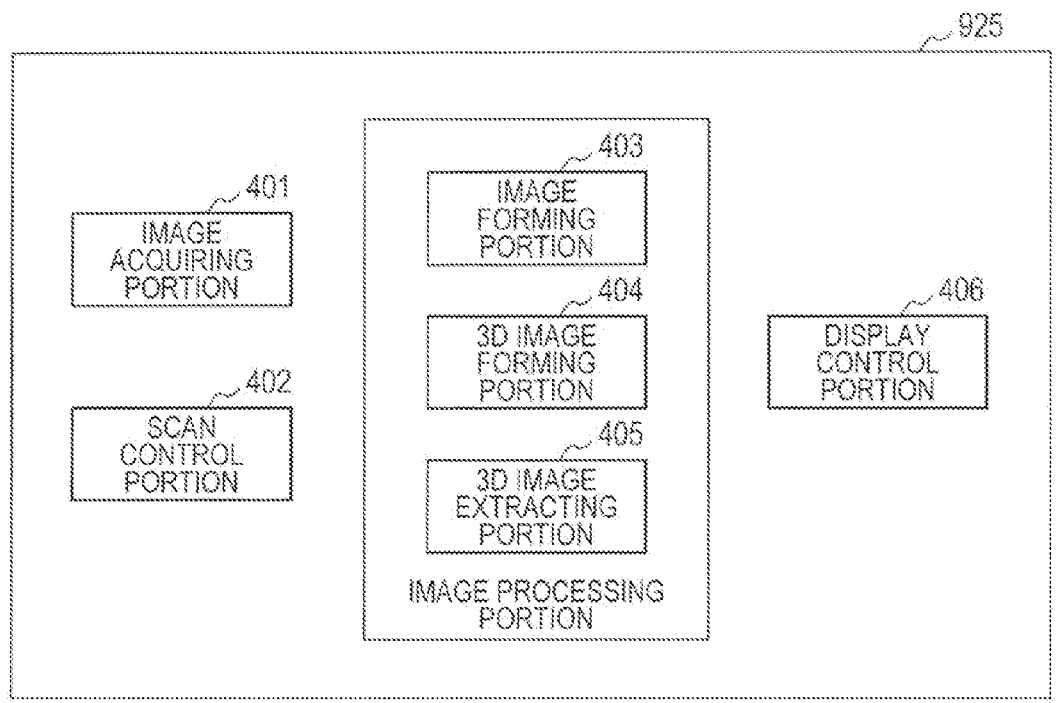
FIG. 10 is a block diagram illustrating a configuration of an image processing apparatus in the first embodiment.

A method of taking a tomographic image with use of the fundus inspecting apparatus 200 is described with reference to a functional block diagram illustrated in FIG. 10. FIG. 10 is a schematic view illustrating the function of the personal computer 925.

The personal computer 925 (specifically, a processor included in the personal computer 925) executes, for example, a program stored in the storage unit 926 to function as an image acquiring portion 401, a scan control portion 402, an image forming portion 403, a 3D image forming portion 404, a 3D image extracting portion 405, and a display control portion 406.

The fundus inspecting apparatus 200 controls the XY scanner 134 to take a tomographic image of a desired part of the fundus of the eye 107 to be inspected. Specifically, the scan control portion 402 controls the XY scanner 134.

An image processing method using the fundus inspecting apparatus 200 is described. When a scan pattern is selected via the input portion 929, regardless of the selected scan pattern, the scan control portion 402 controls the XY scanner 134 to perform raster scan. Then, the image acquiring portion 401 acquires a tomographic image based on a signal received by the line sensor 182. That is, the image acquiring portion 401 serving as an acquiring unit for acquiring a tomographic image group acquires images for forming a 3D tomographic image. Note that, the XY scanner 134 scans the measuring light in an x direction of FIG. 2A, and the line sensor 182 images information a predetermined number of times from an imaging range in the fundus in the x direction.

The fast Fourier transform (FFT) is performed on a luminance distribution obtained on the line sensor 182 at a certain position in the x direction, and a linear luminance distribution obtained by the FFT is converted into density or color information. This converted information is referred to as an A-scan image. After a plurality of A-scan images are taken for organizing one B-scan image, the scan position in a y direction is moved, and the scanning in the x direction is performed again so that a plurality of B-scan images are acquired. That is, a plurality of tomographic images $T_1$ to $T_n$ that are acquired at different positions on the eye to be inspected and extend in parallel to each other are acquired as a tomographic image group. Based on the images acquired by the image acquiring portion 401, the 3D image forming portion 404 forms a 3D image illustrated in FIG. 2B. Note that, in this embodiment, n tomographic images suitable for 3D image formation are obtained, but, for example, the number of the tomographic images to be acquired may be increased or decreased depending on the resolution of the image to be extracted, which is described later.

Next, the 3D image extracting portion 405 extracts an image corresponding to the scan pattern selected by the input portion 929. That is, in the present invention, the 3D image extracting portion 405 functions as a forming unit for forming, based on the tomographic image group including the plurality of tomographic images obtained as the B-scan images, an image arranged so as to intersect with at least one of the plurality of tomographic images. The extracted image is displayed on the display portion 928 by the display control portion (unit) 406 in accordance with a predetermined mode such as one illustrated in FIG. 3. The image forming portion 403 forms a fundus image based on the B-scan images. That is, the image forming portion 403 corresponds to an example of a fundus image acquiring unit for acquiring the fundus image of the eye to be inspected. Further, the 3D image extracting portion 405 corresponds to an example of a tomographic image acquiring unit for acquiring a tomographic image of the fundus in a region (sector).

Figure 3:
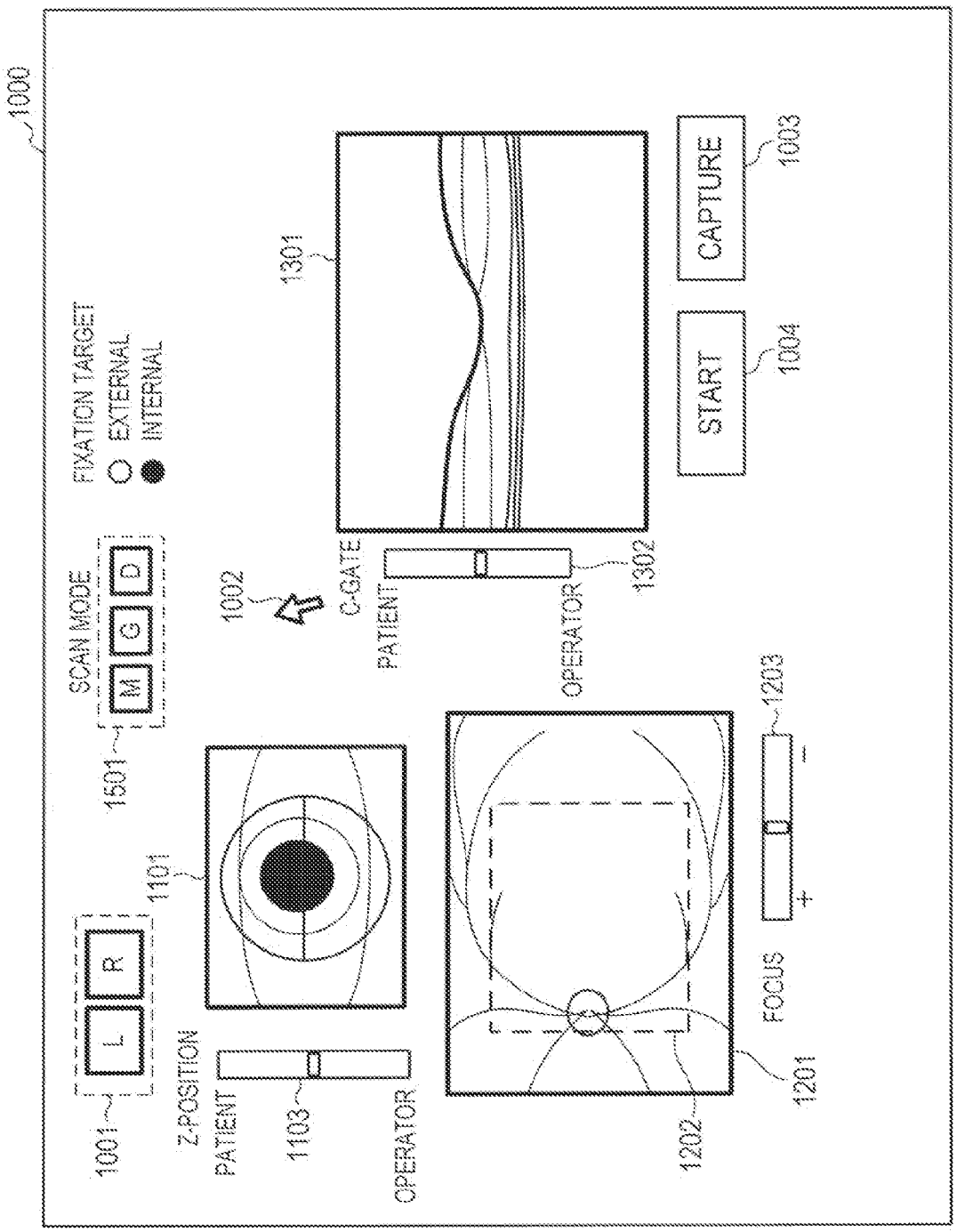
FIG. 3 is a view illustrating an imaging screen in the first embodiment.

FIG. 3 is an example of a screen 1000 to be displayed on the display portion 928. The screen 1000 includes an anterior ocular segment observation image 1101, a fundus observation image 1201, and a tomographic observation image 1301. Further, the screen 1000 includes a left or right eye selecting button 1001. Further, on the fundus observation image 1201, information 1202 representing a range of taking the tomographic image is displayed.

Next, a method of acquiring a tomographic image using the OCT apparatus and a processing method, which are features of this embodiment, are described with reference to FIGS. 1A to 9.

FIG. 9 is a flow chart of the method of acquiring the tomographic image. In Step S1, a scan mode is selected from a scan mode button 1501 in the measurement screen illustrated in FIG. 3. The scan modes include Macula 3D, Glaucoma 3D, and Disc 3D. When the scan modes are switched, the optimum scan pattern and the eye fixing position are set for each of the scan modes. The scan patterns include radial scan, cross scan, circle scan, and 3D scan. In the present invention, those patterns become operation patterns for obtaining an image including a plurality of radially arranged tomographic image groups, an image including two intersecting tomographic image groups, an image including a cylindrical tomographic image group, and an image including a plurality of parallel tomographic image groups, respectively.

In this embodiment, a case where the radial scan is selected as the scan pattern is described. Note that, the scan pattern is not limited to radial scan, and other scan patterns may be selected. In Step S2, a start button 1004 is depressed to automatically perform focus adjustment and alignment adjustment. Thus, imaging is prepared. In order to finely adjust the focus and alignment, a slider 1103 is operated to move and adjust the position of the optical head 900 with respect to the eye to be inspected in a z direction (optical axis direction). Further, a slider 1203 is operated to perform focus adjustment, and a slider 1302 is operated to perform coherence gate position adjustment. The focus adjustment corresponds to adjustment of moving the lenses 135-3 and 135-5 in the directions of the illustrated arrows in order to adjust the focus with respect to the fundus. The coherence gate adjustment corresponds to adjustment of moving the mirror 132-4 in the direction of the illustrated arrow in order to observe the tomographic image at a desired position in the tomographic image displayed screen. Subsequently, in Step S3, a capture button 1003 is depressed to perform imaging. Note that such button depress operation and the like is executed by using a mouse cursor 1002.

Figure 2A:
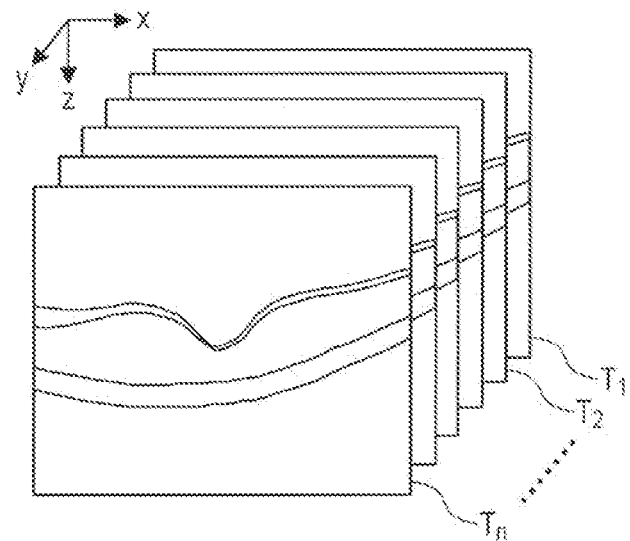
FIGS. 2A and 2B are explanatory views illustrating a 3D image acquiring method in the first embodiment.
Figure 2B:
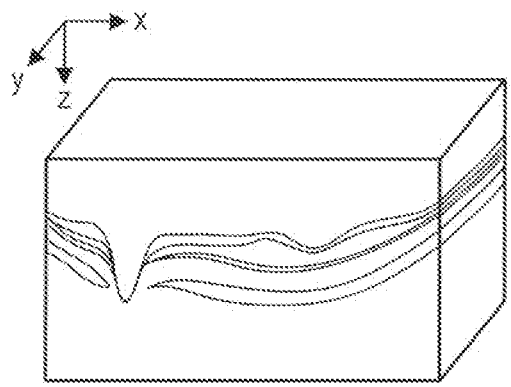
Figure 4:
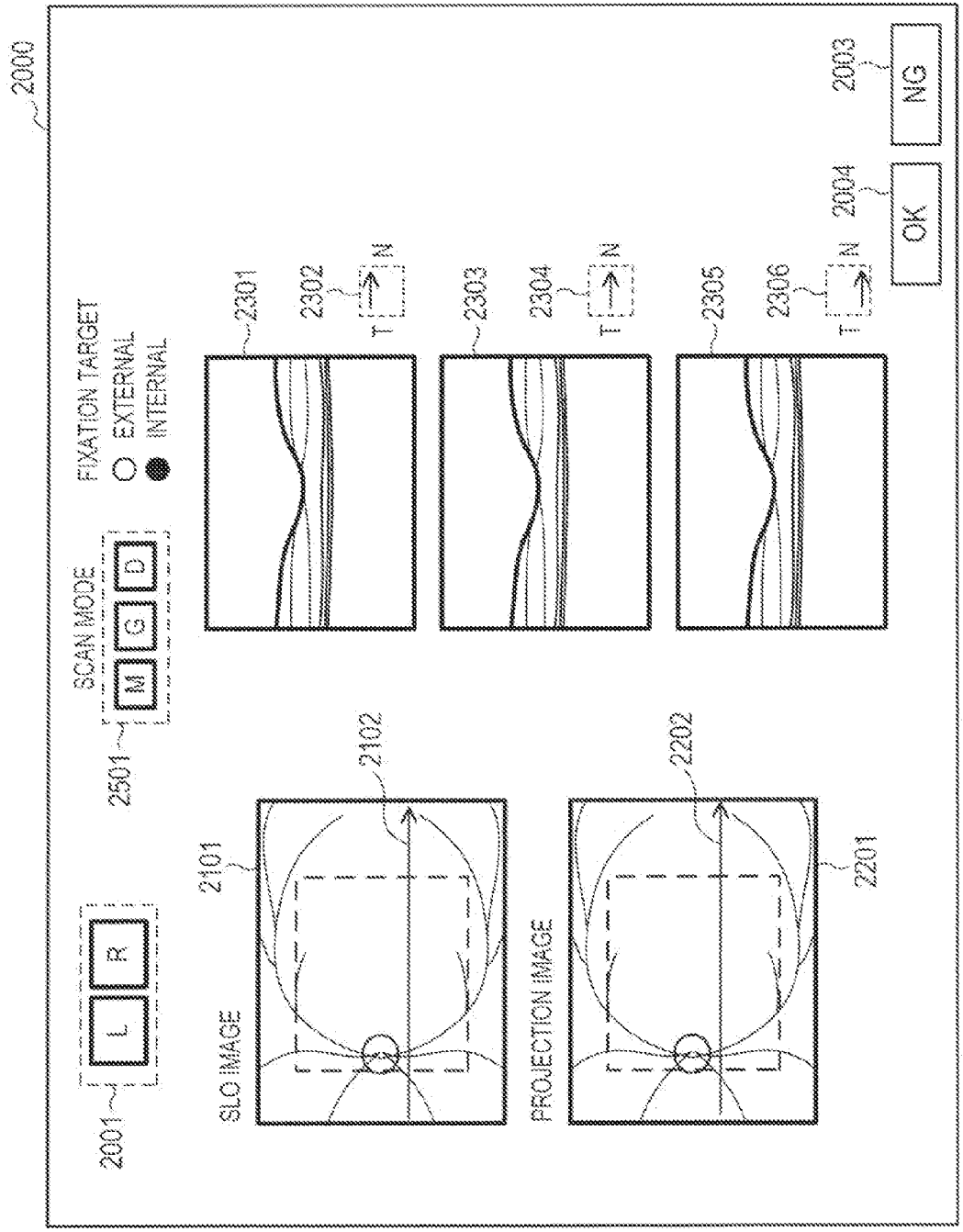
FIG. 4 is a view illustrating a screen displayed after the imaging in the first embodiment.

In Step S4, the XY scanner 134 executes 3D scan. In Step S5, based on the B-scan images illustrated in FIG. 2A, a 3D tomographic image volume illustrated in FIG. 2B is formed. In Step S6, as illustrated in FIG. 4, taken fundus images 2101 and 2201 and tomographic images 2301, 2303, and 2305 are displayed on a screen 2000. The tomographic image 2303 is a tomographic image at scanning lines 2102 and 2202. The scanning lines 2102 and 2202 automatically move in the up-down direction in the scanning range so as to display the corresponding tomographic image. The tomographic image 2301 is a tomographic image at an upper edge of the scanning range, and the tomographic image 2305 is a tomographic image at a lower edge of the scanning range. Further, arrows 2302, 2304, and 2306 represent positions of the tomographic images on the fundus image (tomographic imaging range). Note that, in this embodiment, the fundus image 2101 is an SLO image, and the fundus image 2201 is an integrated image. Further, a left or right eye selecting button 2001 is similar to the left or right eye selecting button 1001 in FIG. 3, and a scan mode button 2501 is similar to the scan mode button 1501 in FIG. 3.

Figure 5:
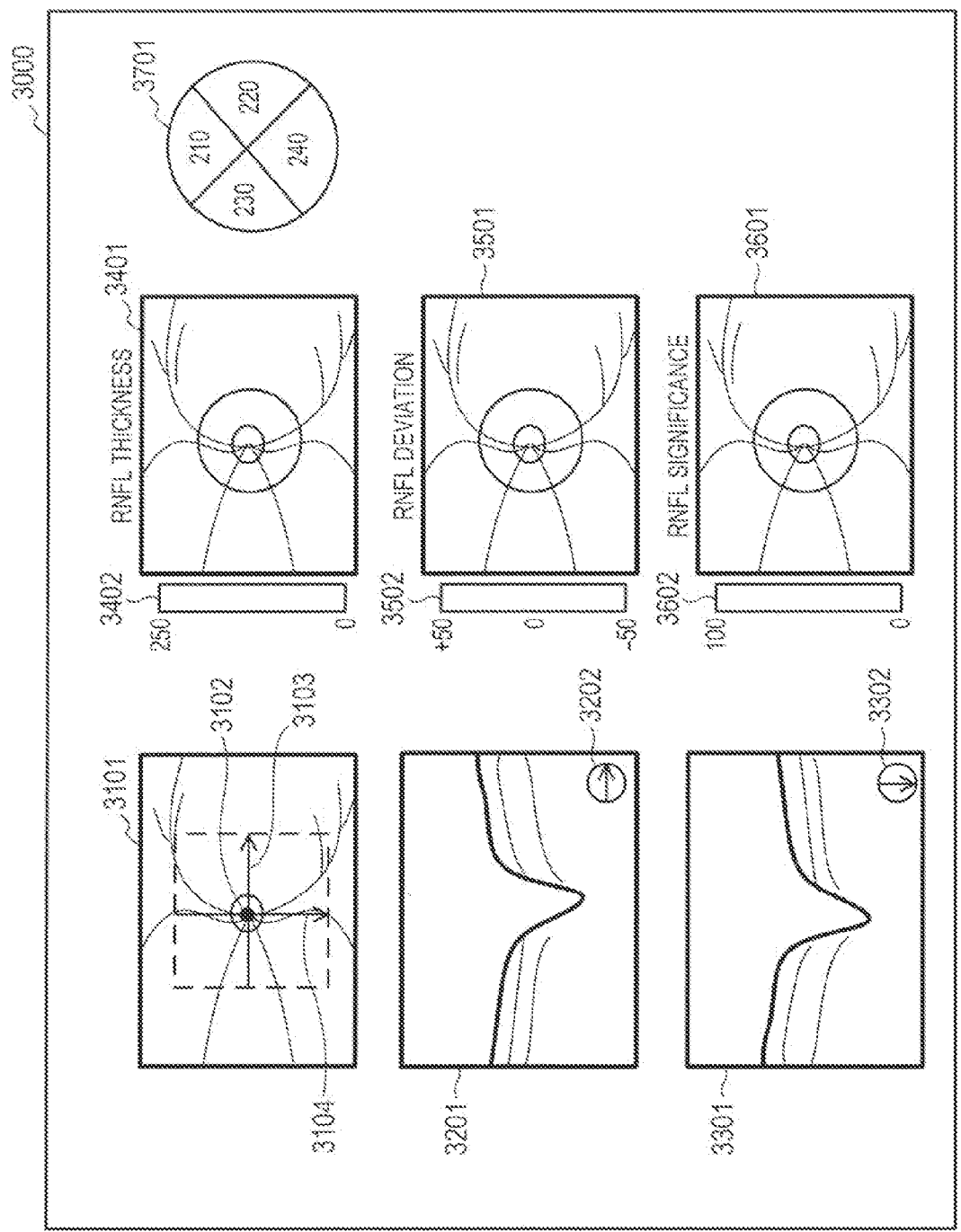
FIG. 5 is a view illustrating a report screen in the first embodiment.

In Step S7, an OK button 2004 or an NG button 2003 is depressed, and a report screen 3000 is formed when the OK button 2004 is depressed (FIG. 5).

The report screen 3000 includes a fundus image 3101. On the fundus image 3101, a main scanning line 3103 and a sub-scanning line 3104 are displayed with a position 3102 designated by the input portion 929 as a center. The report screen 3000 further includes a tomographic image 3201 corresponding to the main scanning line 3103, and a tomographic image 3301 corresponding to the sub-scanning line 3104.

Further, on the tomographic image 3201, information 3202 representing the direction of the main scanning line 3103 is displayed, and on the tomographic image 3301, information 3302 representing the direction of the sub-scanning line 3104 is displayed. Note that, the information 3202 representing the direction of the main scanning line 3103 and the information 3302 representing the direction of the sub-scanning line 3104 may not be displayed on the tomographic images, but may be displayed in the vicinity of the tomographic images.

In Step S9, a given scan center position 3102 is designated on the fundus image 3101 by clicking with a mouse cursor (not shown). This designation is executed by a module region in the display control portion 406, which functions as a center position designating unit for designating a formed image center position corresponding to a center position of a formed image that is formed by the forming unit. In Step S10, coordinates (x, y) 3102 of the position designated in Step S9 are acquired. In Step S11, with the coordinates (x, y) 3102 as a center, the tomographic images taken along the main scanning line 3103 and the sub-scanning line 3104 are formed as a formed image based on the 3D tomographic image. Those main scanning line 3103 and sub-scanning line 3104 correspond to a first-direction line and a second-direction line different from the first-direction line, respectively, which determine the arrangement of the extracting position of the formed image or the like in the fundus image corresponding to a planar image of the object to be inspected in the present invention. The main scanning line 3103 intersects with the formed image at a predetermined position. The predetermined position corresponds to the coordinates (x, y) 3102. Further, determination of those lines is executed by a module region in the display control portion 406, which functions as a formed image position determining unit for determining the first-direction line and the second-direction line intersecting therewith.

In Step S12, based on the 3D tomographic image formed in Step S5, the thickness of the retina is calculated and displayed in a sector form as a retina thickness map 3701, and a retinal nerve fiber layer (RNFL) thickness 3401, RNFL deviation 3501 based on normal eye database (NDB), and RNFL significance 3601 based on NDB are calculated and displayed as maps. Note that, those calculations are performed by, for example, the personal computer 925. That is, the personal computer 925 corresponds to an example of a calculating unit for calculating the thickness of a predetermined layer of the fundus of the eye to be inspected in a partial region on the fundus image.

Further, the RNFL thickness 3401 is displayed so that the thickness can be identified by, for example, colors. The colors corresponding to the thicknesses are represented by a display 3402. Further, the deviation 3501 is displayed so that the deviation can be identified by, for example, colors. The colors corresponding to the deviations are represented by a display 3502. Further, the significance 3601 is displayed so that the significance can be identified by, for example, colors. The colors corresponding to the significances are represented by a display 3602. In this case, the circle near the papilla in each of the RNFL thickness 3401, the RNFL deviation 3501, and the RNFL significance 3601 corresponds to the retina thickness map 3701. Note that, the circle near the papilla in each of the RNFL thickness 3401, the RNFL deviation 3501, and the RNFL significance 3601 is not displayed in four divided parts, but each of the RNFL thickness 3401, the RNFL deviation 3501, and the RNFL significance 3601 is calculated in four divided parts when the retina thickness map 3701 is formed. Note that, the retina thickness map 3701 is not limited to a map divided in four parts, but may be divided into five parts or more or three parts or less.

In Step S13, when a given position on the fundus image 3101 is clicked again by the mouse cursor, the processing in Steps S10, S11, and S12 is performed again, and the tomographic image of the designated position and the retina thickness map are calculated again.

Further, for example, in a case where a mouse wheel is rotated when the mouse cursor is on the fundus image, the main scanning line 3103 and the sub-scanning line 3104 rotate about the scan center position 3102, and corresponding tomographic images 3201 and 3301 are displayed along therewith. Note that, in accordance with the rotation of the main scanning line 3103 and the sub-scanning line 3104, and in addition, in accordance with the rotation direction of the mouse wheel, the information 3202 representing the direction of the main scanning line 3103 and the information 3302 representing the direction of the sub-scanning line 3104 may be similarly rotated. In this way, when the acquiring position of the tomographic image is rotated, it becomes easy to grasp the information on in which direction the tomographic image is acquired on the fundus image 3101, which has been difficult to grasp in a conventional case.

Note that, the rotating directions of the main scanning line 3103 and the sub-scanning line 3104 may be any one of clockwise and counterclockwise.

Further, on the fundus image 3101 in FIG. 5, the tomographic imaging range is represented by broken lines, and the main scanning line 3103 and the sub-scanning line 3104 move in accordance with the rotation of the mouse wheel within the range represented by the broken lines. Note that, in the rectangular imaging range represented by the broken lines, the length of the tomographic image, which can be obtained when the main scanning line 3103 or the sub-scanning line 3104 is located on the diagonal of the imaging range, is larger than the length of the tomographic image, which can be obtained when the main scanning line 3103 or the sub-scanning line 3104 is located at a position different from the diagonal of the imaging range. Therefore, the lengths of the main scanning line 3103 and the sub-scanning line 3104 are set to not change during rotation. Alternatively, the lengths of the main scanning line 3103 and the sub-scanning line 3104 may be set to depend on the range represented by the broken lines, and when the tomographic image becomes long, the end portion of the tomographic image may not be displayed to constantly display the tomographic image having substantially the same length. Still alternatively, the lengths of the main scanning line 3103 and the sub-scanning line 3104 may be set to depend on the range represented by the broken lines, and when the tomographic image becomes long, the tomographic image may be displayed in a size reduced in accordance with the display region, or the display region itself may be increased.

Note that, the fundus image 3101 may be an image obtained by integrating 3D tomographic images or may be an SLO image.

Note that, formation of a sector with respect to the tomographic image at a designated position, which corresponds to the formed image, and display of the map of the thickness of the predetermined layer of the object to be inspected in the region sectioned by the sector based on the tomographic image group are executed by a module region in the image forming portion 403, which functions as a sector forming unit. Further, the sector forming unit recalculates the thickness of the predetermined layer such as a retina layer to be displayed as a map in accordance with the alignment of the center position of the sector, and the display control portion 406 displays the recalculation result on the display portion 928 together with the tomographic images.

In this embodiment, when the fundus is scanned, 3D scan is performed in any scan pattern, and hence a tomographic image of a desired part can be extracted from the 3D tomographic image. Conventionally, there has been cases where a tomographic image of an intended part cannot be acquired in a scan pattern (radial scan, circle scan, cross scan, or the like) in which only a tomographic image taken along a designated scanning line is acquired, but also in those cases, any one of those tomographic images can be easily regenerated as the formed image. Note that, the formed image may be a single tomographic image taken along a specific line. Further, 3D scan is performed, no matter which scan pattern is selected, and hence the trajectory of the scanning line is constant. Therefore, fluctuations in eye fixation depending on the scanning line can be eliminated.

That is, with the above-mentioned configuration, no matter which scan pattern is selected, 3D scan is performed to acquire the 3D tomographic image, and the tomographic image of the scan pattern can be extracted. Conventionally, there have been cases where a tomographic image of an intended part cannot be acquired in a scan pattern (radial scan, circle scan, cross scan, or the like) in which only a tomographic image taken along a designated scanning line is acquired, but also in those cases, the tomographic image of the desired part can be easily regenerated. Further, 3D scan is performed in any scan pattern, and hence the trajectory of the scanning line is constant. Therefore, fluctuations in eye fixation depending on the scanning line can be eliminated.

Second Embodiment

Figure 6:
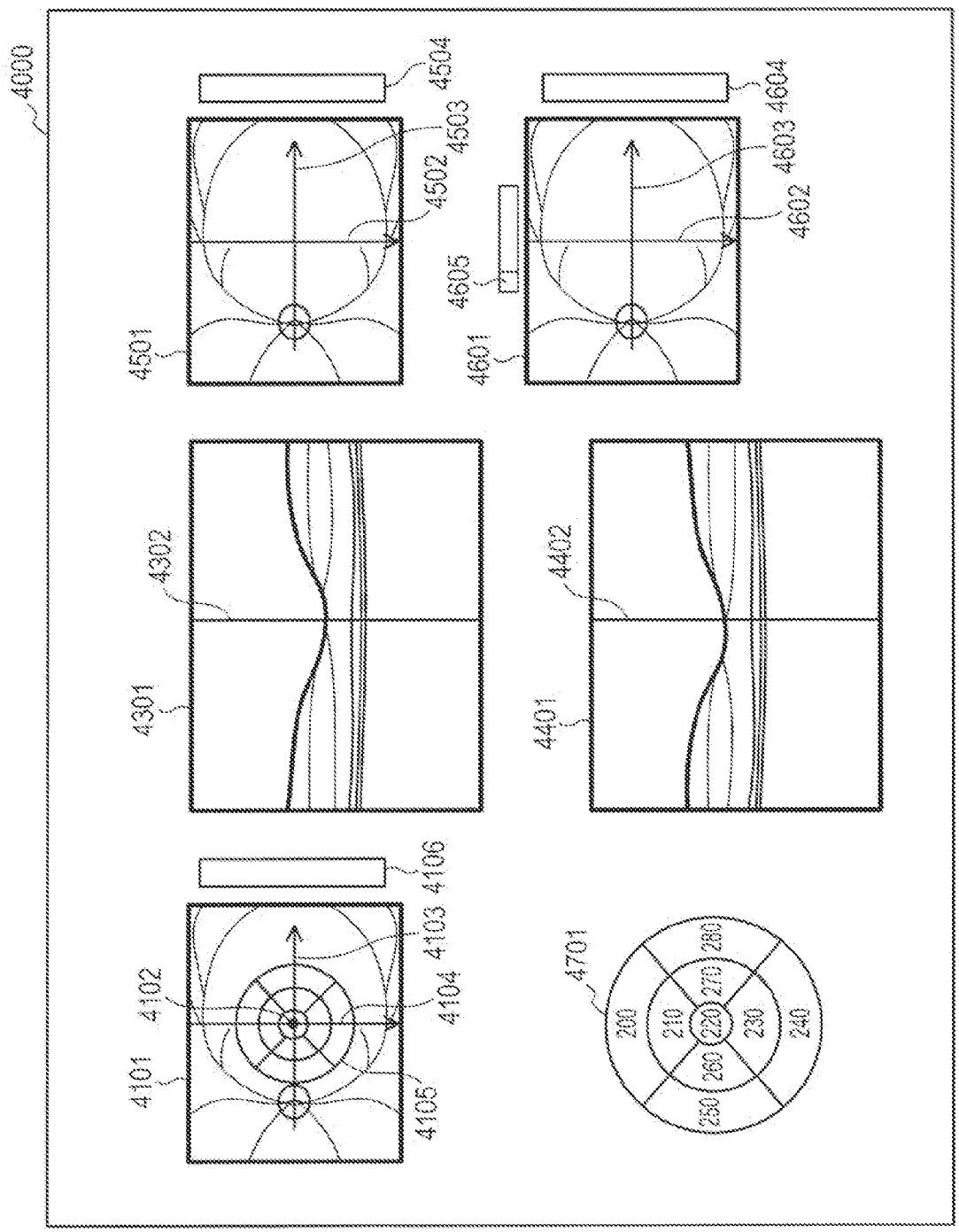
FIG. 6 is a view illustrating a report screen in a second embodiment of the present invention.

A second embodiment of the present invention and the first embodiment employ the same method of acquiring a tomographic image but differ in report screen. Note that, the report screen to be displayed is different depending on, for example, the scan mode selected in the screen of FIG. 3. For example, FIG. 5 illustrates the report screen when a papilla imaging mode is selected in the scan mode button 1501. Further, for example, FIG. 6 illustrates the report screen when a macula imaging mode is selected in the scan mode button 1501. A report screen 4000 illustrated in FIG. 6 includes a fundus image 4101. On the fundus image 4101, a main scanning line 4103, a sub-scanning line 4104, and a sector 4105 are displayed. Note that, in an initial state of displaying the report screen 4000, for example, the center of the sector 4105 matches with the center of the tomographic imaging range.

Further, the intersection 4102 between the main scanning line 4103 and the sub-scanning line 4104 matches with, for example, the center of the sector 4105. The report screen 4000 includes a main scanning line tomographic image 4301 serving as a tomographic image corresponding to the main scanning line 4103, a sub-scanning line tomographic image 4401 serving as a tomographic image corresponding to the sub-scanning line 4104, and a thickness map 4701. Note that, the shape of the sector 4105 is not limited to that illustrated in FIG. 6, and may be other shapes. Note that, also in the second embodiment, the function of the personal computer is substantially similar to that illustrated in FIG. 10, and hence detailed description thereof is omitted.

Also in the second embodiment, the tomographic image is acquired in accordance with the flow chart of the method of acquiring the tomographic image illustrated in FIG. 9. The acquired tomographic image is displayed on the report screen 4000 as illustrated in FIG. 6. That is, the display control portion 406 corresponds to an example of a display control unit for causing the display unit to display a fundus image, a display form representing a region, and a tomographic image.

Figure 7A:
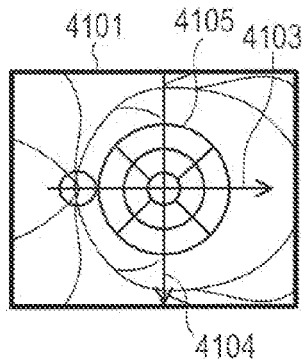
FIGS. 7A, 7B and 7C are explanatory views relating to a fundus image in the second embodiment.
Figure 7B:
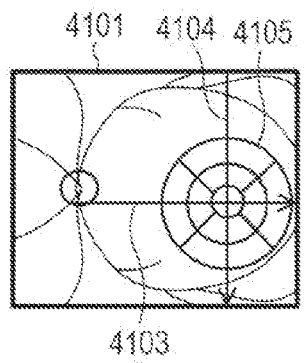

Now, the main scanning line 4103, the sub-scanning line 4104, and the sector 4105, which are displayed on the fundus image 4101 corresponding to a planar image of the object to be inspected, are described. When a given scan center position is clicked by a mouse cursor from the initial position of FIG. 7A, as illustrated in FIG. 7B, the sector 4105 is moved under a state in which the intersection between the main scanning line 4103 and the sub-scanning line 4104 and the center position of the sector 4105 for sectioning the formed image match with each other. That is, along with the movement of the sector 4105, the tomographic image displayed on the report screen 4000 is changed. Further, the input portion 929 such as the mouse cursor corresponds to an example of a changing unit for changing the position of a display form representing the region displayed on the display unit. As illustrated in FIG. 7B, along with the movement of the sector 4105, the main scanning line 4103 and the sub-scanning line 4104 move. Therefore, when the position of the display form representing the region is changed, the 3D image extracting portion 405 serving as the tomographic image acquiring unit acquires a tomographic image of the fundus of the eye to be inspected in the region after the position is changed. Then, the display control unit causes the display unit to display the tomographic image of the region after the position is changed instead of the tomographic image in the region before the position is changed.

Figure 7C:
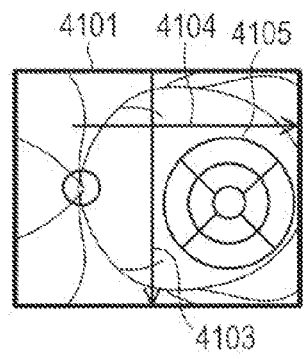

Further, when the main scanning line 4103 and the sub-scanning line 4104 are selected by clicking with the mouse cursor and dragged as illustrated in FIG. 7C, the sector does not move but the main scanning line 4103 and the sub-scanning line 4104 can be moved. While viewing the main scanning line tomographic image 4301 and the sub-scanning line tomographic image 4401 corresponding to the main scanning line 4103 and the sub-scanning line 4104, respectively, the main scanning line 4103 and the sub-scanning line 4104 are moved. In this manner, the main scanning line 4103 and the sub-scanning line 4104 can be located at positions at which the fovea is most recessed, to thereby accurately find the center of the fovea.

At this time, when the intersection between the main scanning line and the sub-scanning line is clicked with the mouse cursor, the center of the sector matches with the intersection between the main scanning line 4103 and the sub-scanning line 4104, and thus the sector can be accurately moved to the center of the fovea. With this, an accurate retina thickness map 4701 can be obtained with the fovea as the center of the thickness map, which is useful for diagnosis of the retina. That is, a predetermined layer in an image sectioned by a sector for sectioning an image, in this embodiment, the thickness of the retina is displayed on the display portion 928 by the display control portion 406. Further, designation of arrangement of such an image including the tomographic images in the fundus image is executed by a module region in the display control portion 406, which functions as a position designating unit.

Note that, the sub-scanning line tomographic image 4401 is formed based on the main scanning line tomographic image 4301, and hence the sub-scanning line tomographic image 4401 is generally deteriorated in image quality as compared to the main scanning line tomographic image 4301. In some cases, it is difficult to accurately find the center of the fovea by viewing this tomographic image. In such cases, an auxiliary tomographic line 4302 displayed on the main scanning line tomographic image 4301 may be used to accurately find the center of the fovea. The auxiliary tomographic line 4302 is located at the same tomographic position as the sub-scanning line 4104, and when the auxiliary tomographic line 4302 is moved, sub-scanning lines 4104 and 4502 are moved in association therewith. In order to accurately obtain the retina thickness map 4701, the main scanning line 4103 is moved while viewing the main scanning line tomographic image 4301 to find the position at which the fovea is most recessed, and next the auxiliary tomographic line 4302 is moved to locate the auxiliary tomographic line 4302 to the position at which the fovea is most recessed. At this time, when the intersection between the main scanning line 4103 and the sub-scanning line 4104 is clicked with the mouse cursor, the center of the sector 4105 for sectioning the fundus image or the formed image matches with the intersection between the main scanning line and the sub-scanning line. Thus, the sector 4105 can be accurately moved to the center of the fovea. That is, the sector, the main scanning line, and the sub-scanning line follow each other. At this time, the sub-scanning line tomographic image 4401 is unnecessary, and hence the sub-scanning line tomographic image 4401 may not be displayed. Further, when the sub-scanning line tomographic image 4401 is not displayed, in the region in which the sub-scanning line tomographic image 4401 has been displayed, the tomographic image in the vicinity of the fovea of the main scanning line tomographic image 4301 may be displayed in an enlarged manner and further the auxiliary tomographic line 4302 may be displayed. With this, the center of the fovea can be found more accurately. Note that, a switch may be provided on the report screen 4000 for switching the display to non-display of the sub-scanning line tomographic image 4401. Further, a fundus image 4501 displays a color map of the deviation or the significance of the RNFL based on the NDB. When a retina thickness switching button 4605 is depressed, a fundus image 4601 switches the thickness map among thickness maps for the retinal pigment epithelium layer (RPE), the photoreceptor inner/outer segment (IS/OS), and (the retinal nerve fiber layer: RNFL)+(the ganglion cell layer: GCL)+(the inner plexiform layer:IPL), and the corresponding thickness map is displayed as a color map. Note that, when an auxiliary tomographic line 4402 is moved, main scanning lines 4103 and 4503 may move in association therewith. In this case, displays 4106, 4504, and 4604 represent colors with respect to the values of the thickness, etc.

In the embodiment described above, the example in which, when the auxiliary tomographic line 4302 is moved, the sub-scanning lines 4104 and 4502 move in association therewith is described. Alternatively, for example, when the sub-scanning line 4104 is moved, the auxiliary tomographic line 4302 and the sub-scanning line 4502 may move in association therewith. That is, the auxiliary tomographic line 4302 and the sub-scanning lines 4104 and 4502 may move in association with each other. The auxiliary tomographic line 4402 and the main scanning lines 4103 and 4503 may similarly move in association with each other. Further, a main scanning line 4603 and a sub-scanning line 4602 may move in association with the auxiliary tomographic line 4402 and the auxiliary tomographic line 4302, respectively.

Figure 8A:
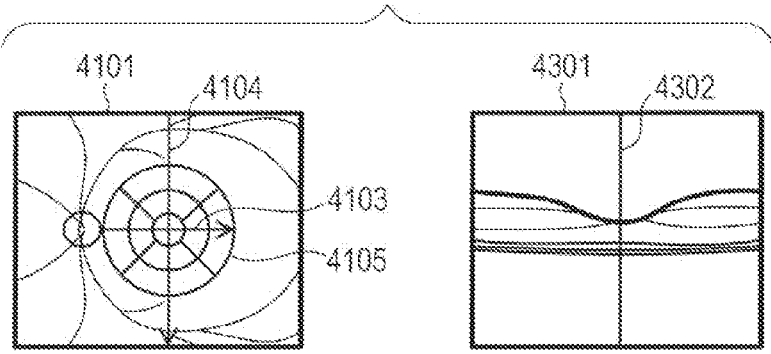
FIGS. 8A and 8B are explanatory views relating to the fundus image in the second embodiment.
Figure 8B:
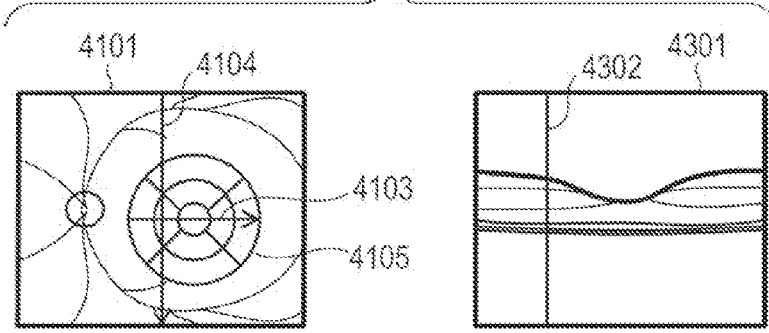

FIGS. 8A and 8B illustrate a modified example. As illustrated in FIGS. 8A and 8B, the main scanning line and the sector are integrated to each other, and the sub-scanning line is independently moved. While viewing the tomographic image, the main scanning line and the sector that are integrated to each other are moved to be located at a position at which the fovea is most recessed. Next, the auxiliary tomographic line in the tomographic image is moved to be located at the position at which the fovea is most recessed. Also in this way, the sector can be accurately moved to the center of the fovea.

Other Embodiment

Further, the present invention can also be realized by performing the following processing. That is, the processing involves supplying software (program) for realizing the functions of the above-mentioned embodiments to a system or an apparatus via a network or various storage media and causing a computer (or a CPU, an MPU, or the like) of the system or the apparatus to read and execute the program.

The present invention is not limited to the above-mentioned embodiments and can be variously modified or changed within a scope without departing from the spirit of the present invention. For example, in the above-mentioned embodiments, the case where an object to be inspected is an eye has been described, but the present invention can also be applied to objects to be measured such as a skin and an organ except an eye. In this case, the present invention has an aspect as medical equipment such as an endoscope except an ophthalmic apparatus. Therefore, it is desired that the present invention be understood as an inspecting apparatus exemplified by an ophthalmologic apparatus, and the eye to be inspected be understood as one aspect of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190592, filed Aug. 30, 2012, which is hereby incorporated by reference herein in its entirety.

What is claimed is:

1. An image processing apparatus, comprising:
a fundus image acquiring unit for acquiring a fundus image of an eye to be inspected;
a calculating unit for calculating a thickness of a predetermined layer of a fundus of the eye to be inspected in a part of a two-dimentional region on the fundus image;
a tomographic image acquiring unit for acquiring a tomographic image of the fundus in the two-dimensional region;
a display control unit for causing a display unit to display the fundus image, a display form representing the two-dimensional region, and the tomographic image; and
a changing unit for changing a position of the display form representing the two-dimensional region, the display form being displayed on the display unit,
the tomographic image acquiring unit being configured to acquire, when the position of the display form representing the two-dimensional region is changed, a tomographic image of the fundus of the eye to be inspected in the two-dimensional region after the position is changed, and
the display control unit being configured to cause the display unit to display the tomographic image in the two-dimensional region after the position is changed instead of the tomographic image in the two-dimensional region before the position is changed.

2. An image processing apparatus, comprising:
an acquiring unit for acquiring a tomographic image group including a plurality of tomographic images that are acquired at different positions of an object to be inspected;
a forming unit for forming, based on the tomographic image group, as a formed image, an image arranged so as to intersect with at least one of the plurality of tomographic images;
a sector forming unit for forming, based on the tomographic image group, a sector for sectioning the formed image, and displaying, as a map, a thickness of a predetermined layer of the object to be inspected in a region sectioned by the sector;
a display control unit for causing a display unit to display the formed image and the sector;
a position designating unit for designating a formed image position serving as a position of the formed image of the object to be inspected; and
an aligning unit for aligning the formed image position and a center position of the sector for sectioning the formed image,
the sector forming unit being configured to recalculate the thickness of the predetermined layer to be displayed as a map in accordance with the alignment of the center position of the sector, and to cause the display unit to display the map.

3. An image processing apparatus according to claim 2, wherein the forming unit is configured to form, as the formed image, any one of an image including a plurality of radially arranged tomographic image groups, an image including a cylindrical tomographic image group, an image including two intersecting tomographic image groups, and an image including a plurality of parallel tomographic image groups, the any one of the images being arranged in a region in which the tomographic image group is obtained.

4. An image processing apparatus according to claim 2, further comprising a formed image position determining unit for determining a first-direction line that intersects with the formed image at a predetermined position to determine arrangement of the formed image, and a second-direction line intersecting with the first-direction line.

5. An image processing apparatus according to claim 3, further comprising a formed image position determining unit for determining a first-direction line that intersects with the formed image at a predetermined position to determine arrangement of the formed image, and a second-direction line intersecting with the first-direction line,
the predetermined position comprising a center position of the any one of the image including the plurality of radially arranged tomographic image groups, the image including the cylindrical tomographic image group, the image including the two intersecting tomographic image groups, and the image including the plurality of parallel tomographic image groups.

6. An image processing apparatus according to claim 2, further comprising a position designating unit for designating arrangement of the formed image in a planar image of the object to be inspected,
wherein the display control unit is configured to cause the display unit to display, in the planar image of the object to be inspected, a first-direction line, a second-direction line intersecting with the first-direction line, and the sector for sectioning the planar image,
wherein the first-direction line is equal in direction to a layer of the object to be inspected from which the formed image is obtained, and
wherein the aligning unit is configured to cause the first-direction line and the second-direction line to follow the sector for sectioning the planar image.

7. An image processing apparatus according to claim 6, wherein the position designating unit is configured to designate the arrangement of the formed image based on the position of the formed image.

8. An image processing apparatus according to claim 6, wherein the display control unit is configured to:
cause the display unit to display the second-direction line in a tomographic image taken along the first-direction line; and
cause the display unit to display the first-direction line in a tomographic image taken along the second-direction line.

9. An image processing method, comprising:
acquiring a tomographic image group including a plurality of tomographic images that are acquired at different positions of an object to be inspected and extend in parallel to each other;
forming, as a formed image, an image arranged so as to intersect with at least one of the plurality of tomographic images, based on the tomographic image group;
forming a sector for sectioning the formed image, and for displaying, as a map, a thickness of a predetermined layer of the object to be inspected in a region sectioned by the sector, based on the tomographic image group;
causing a display unit to display the formed image and the sector; and
aligning a formed image position serving as a designated position of the formed image of the object to be inspected and a center position of the sector for sectioning the formed image,
the forming a sector comprising recalculating the thickness of the predetermined layer to be displayed as a map in accordance with the alignment of the center position of the sector, and causing the display unit to display the map.

10. A recording medium for recording a program for causing a computer to execute respective steps of the image processing method according to claim 9.

11. An image processing apparatus comprising:
an acquiring unit for acquiring a group of tomographic images including a plurality of tomographic images acquired at different positions on a fundus of an eye to be inspected;
a display control unit for causing a display unit to display a figure wherein an interior of the figure is divided into a plurality of areas by lines, while overlapping the figure on the fundus image of the eye to be inspected;
a tomographic image acquiring unit for acquiring the tomographic image at a position on the fundus image where the figure is displayed, based on the group of tomographic images; and
a calculating unit for calculating a thickness of a predetermined layer of the fundus for each of the plurality of areas in the figure, based on the group of tomographic images,
wherein the tomographic image acquiring unit acquires a new tomographic image at a position on the fundus image where the figure is displayed, based on the group of tomographic images, in a case that the displayed position of the figure is changed, and
wherein the calculating unit newly calculates the thickness of the predetermined layer based on the group of tomographic images, in the case that the displayed position of the figure is changed.

12. An image processing apparatus according to claim 11, wherein the display control unit causes the display unit to display the thickness of the predetermined layer, calculated by the calculating unit, for each of the plurality of areas.

13. An image processing apparatus according to claim 11, wherein the calculating unit calculates an average value of the thickness of the predetermined layer, for each of the areas in the figure.

14. An image processing apparatus according to claim 13, wherein the display control unit cause the display unit to display the average value of the predetermined layer calculated by the calculating unit for each of the plurality of areas.

15. An image processing apparatus according to claim 11, wherein the display control unit causes the display unit, in a case that a predetermined position on the fundus image is selected, to change the displayed position of the figure to the selected position.

16. An image processing apparatus according to claim 15, wherein the display control unit causes the control unit to change the displayed position of the figure so as to match the selected position with a center of the figure.

17. An image processing apparatus according to claim 11, wherein in a case that the displayed position of the figure is changed the display control unit causes the display unit to display a tomographic image newly acquired by the tomographic image acquiring unit after changing the displayed position of the figure, in place of the tomographic image displayed by the display unit before changing the displayed position of the figure.

18. An image processing apparatus according to claim 11, wherein the tomographic image acquiring unit acquires two tomographic images which include a center position of the figure on the fundus image and are orthogonal to each other.

19. An image processing apparatus according to claim 11, wherein the display control unit causes the display unit to display on the fundus image a designation line designating a position on the fundus image, of the tomographic image acquired by the tomographic image acquiring unit.

20. An image processing apparatus according to claim 19, wherein the display control unit causes the display unit to change the displayed position of the designation line in accordance with a change of the displayed position of the figure.

21. An image processing apparatus according to claim 11, wherein the figure is a circle.

22. An image processing method comprising:
acquiring a group of tomographic images including a plurality of tomographic images acquired at different positions on a fundus of an eye to be inspected;

causing a display unit to display a figure wherein an inside of the figure is divided into a plurality of areas by lines, while overlapping the figure on the fundus image of the eye to be inspected;

acquiring the tomographic image at a position on the fundus image where the figure is displayed, based on the group of tomographic images; and calculating a thickness of a predetermined layer of the fundus for each of the plurality of areas in the figure, based on the group of tomographic images, wherein in the acquiring, a new tomographic image at a position on the fundus image where the figure is displayed is acquired based on the group of tomographic images, in a case that the displayed position of the figure is changed, and wherein in the calculating, the thickness of the predetermined layer is newly calculated based on the group of tomographic images, in the case that the displayed position of the figure is changed.

23. A recording medium for recording a program which causes a computer to execute the respective steps of the image processing method according to claim 22.

24. An image processing apparatus comprising:

an acquiring unit for acquiring a group of tomographic images including a plurality of tomographic images acquired at different positions on a fundus of an eye to be inspected;

a display control unit for causing a display unit to display a figure wherein an inside of the figure is divided into a plurality of areas by lines, while overlapping the figure on the fundus image of the eye to be inspected; and a calculating unit for calculating a thickness of a predetermined layer of the fundus for each of the plurality of areas in the figure, based on the group of tomographic images, wherein the calculating unit newly calculates the thickness of the predetermined layer based on the group of tomographic images, in the case that the displayed position of the figure is changed.

25. An image processing apparatus according to claim 24, wherein the display control unit causes the display unit to display the thickness of the predetermined layer, calculated by the calculating unit, for each of the plurality of areas.

26. An image processing apparatus according to claim 24, wherein the calculating unit calculates an average value of the thickness of the predetermined layer, for each of the areas in the figure.

27. An image processing apparatus according to claim 26, wherein the display control unit causes the display unit to display the average value of the predetermined layer calculated by the calculating unit for each of the plurality of areas.

28. An image processing apparatus according to claim 24, wherein the display control unit causes the display unit, in a case that a predetermined position on the fundus image is selected, to change the displayed position of the figure to the selected position.

29. An image processing apparatus according to claim 24, further comprising a tomographic image acquiring unit for acquiring a tomographic image at a predetermined position in the fundus image, based on the group of the tomographic images, wherein the display control unit causes the display unit to display on the fundus image a designation line designating a position on the fundus image, of the tomographic image acquired by the tomographic image acquiring unit.

30. An image processing apparatus according to claim 29, wherein the display control unit causes the display unit to change the displayed position of the designation line in accordance with a change of the displayed position of the figure.

31. An image processing apparatus according to claim 29, wherein the display control unit causes the display unit to change the displayed position of the designation line independent from the change of the displayed position of the figure.

32. An image processing apparatus according to claim 24, wherein the figure is a circle.

33. An image processing apparatus comprising:

an acquiring unit for acquiring a group of tomographic images including a plurality of tomographic images acquired at different positions on a fundus of an eye to be inspected;

a display control unit for causing a display unit to display a figure wherein an inside of the figure is divided into a plurality of areas by lines, while overlapping the figure on the fundus image of the eye to be inspected;

a tomographic image acquiring unit for acquiring the tomographic image at a position on the fundus image where the figure is displayed, based on the group of tomographic images; and a calculating unit for calculating a thickness of a predetermined layer of the fundus for each of the plurality of areas in the figure, based on the group of tomographic images, wherein the tomographic image acquiring unit acquires a new tomographic image at a position on the fundus image where the figure is displayed, based on the group of tomographic images, in a case that the displayed position of the figure is changed.

34. An image processing apparatus according to claim 33, wherein the display control unit causes the display unit to display the thickness of the predetermined layer, calculated by the calculating unit, for each of the plurality of areas.

35. An image processing apparatus according to claim 33, wherein the calculating unit calculates an average value of the thickness of the predetermined layer, for each of the areas in the figure.

36. An image processing apparatus according to claim 35, wherein the display control unit causes the display unit to display the average value of the thickness of the predetermined layer calculated by the calculating unit for each of the plurality of areas.

37. An image processing apparatus according to claim 33, wherein the display control unit causes the display unit, in a case that a predetermined position on the fundus image is selected, to change the displayed position of the figure to the selected position.

38. An image processing apparatus according to claim 33, wherein the display control unit causes the display unit to display on the fundus image a designation line designating a position on the fundus image, of the tomographic image acquired by the tomographic image acquiring unit.

39. An image processing apparatus according to claim 38, wherein the display control unit causes the display unit to change the displayed position of the designation line in accordance with a change of the displayed position of the figure.

40. An image processing apparatus according to claim 33, wherein the figure is a circle.

* * * * *